(12) United States Patent
Aoki

(10) Patent No.: US 11,686,743 B2
(45) Date of Patent: Jun. 27, 2023

(54) INFORMATION PROCESSING DEVICE, INFORMATION PROCESSING METHOD, AND STORAGE MEDIUM

(71) Applicant: HONDA MOTOR CO., LTD., Tokyo (JP)

(72) Inventor: Haruo Aoki, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 126 days.

(21) Appl. No.: 16/896,270

(22) Filed: Jun. 9, 2020

(65) Prior Publication Data

US 2020/0393490 A1 Dec. 17, 2020

(30) Foreign Application Priority Data

Jun. 11, 2019 (JP) .............................. JP2019-108446

(51) Int. Cl.
*A61B 5/11* (2006.01)
*G01P 15/18* (2013.01)

(52) U.S. Cl.
CPC .................................. *G01P 15/18* (2013.01)

(58) Field of Classification Search
CPC ...... G01P 15/18; A61B 5/7242; A61B 5/1114; A61B 5/1121; A61B 2562/0219; A61B 2562/04; A61B 5/1107; A61B 5/1118; A61B 5/02055; A61B 5/024; A61B 5/1116; A61B 5/1126; A61B 5/6801; A61B 5/72; A61B 5/7235; G06F 17/13; G06F 17/16
See application file for complete search history.

(56) References Cited

U.S. PATENT DOCUMENTS

| 4,650,204 A * | 3/1987 | Bothwell | B62J 17/065 |
| | | | 296/78.1 |
| 2003/0018283 A1 | 1/2003 | Dariush | |
| 2005/0209534 A1* | 9/2005 | Dariush | G09B 23/30 |
| | | | 600/595 |

(Continued)

FOREIGN PATENT DOCUMENTS

| JP | 4264345 | 5/2009 |
| JP | 4392448 | 1/2010 |

(Continued)

OTHER PUBLICATIONS

Glonek et al. Hybrid Orientation Based Human Limbs Motion Tracking Method, pp. 1-22 (Year: 2017).*

(Continued)

*Primary Examiner* — Eyob Hagos
(74) *Attorney, Agent, or Firm* — Amin, Turocy & Watson, LLP

(57) ABSTRACT

Provided is an information processing device including: a storage device having a program stored therein; and a hardware processor, wherein the hardware processor executes the program stored in the storage device to: acquire first data for a dimension of position relating to an object represented in a generalized coordinate system; acquire at least second data for a dimension of acceleration from a plurality of inertial sensors attached to the object; and convert the second data into third data for a dimension of acceleration represented in the generalized coordinate system on the basis of the first data.

4 Claims, 9 Drawing Sheets

(56) References Cited

U.S. PATENT DOCUMENTS

| | | | |
|---|---|---|---|
| 2008/0188907 A1* | 8/2008 | Aguirre-Ollinger | A61H 3/00 601/5 |
| 2008/0221487 A1* | 9/2008 | Zohar | A61B 5/1127 600/595 |
| 2008/0223131 A1 | 9/2008 | Vannucci et al. | |
| 2010/0030532 A1* | 2/2010 | Arora | G06T 13/40 703/2 |
| 2011/0082566 A1* | 4/2011 | Herr | H02K 7/06 623/24 |
| 2016/0113831 A1* | 4/2016 | Hollander | A61H 3/00 623/32 |
| 2019/0056422 A1 | 2/2019 | Park et al. | |

FOREIGN PATENT DOCUMENTS

| | | |
|---|---|---|
| JP | 4764431 | 9/2011 |
| JP | 4806447 | 11/2011 |
| JP | 4981786 | 7/2012 |
| WO | 2006/078553 | 7/2006 |
| WO | 2006/078566 | 7/2006 |
| WO | 2006/107716 | 10/2006 |
| WO | 2006/110895 | 10/2006 |

OTHER PUBLICATIONS

Y. Nakamura, K. Yamane, I. Suzuki, and Y. Fujita: "Dynamics Computation of Musculo-Skeletal Human Model Based on Efficient Algorithm for Closed Kinematic Chains," Proceedings of the 2nd International Symposium on Adaptive Motion of Animals and Machines, Kyoto, Japan, SaP-I-2, Mar. 2003.

R. Fluit et al., "Prediction of ground reaction forces and moments during various activities of daily living," Journal of Biomechanics, p. 9, 2014.

A. Karatsidis, G. Bellusci, H. Schepers, M. de Zee, M. Andersen, and P. Veltink, "Estimation of Ground Reaction Forces and Moments During Gait Using Only Inertial Motion Capture," Sensors, vol. 17, No. 12, p. 75, Dec. 2016.

M. L. Felis, K. Mombaur, and A. Berthoz, "An optimal control approach to reconstruct human gait dynamics from kinematic data," in 2015 IEEE-RAS 15th International Conference on Humanoid Robots (Humanoids), Seoul, South Korea, 2015.

Extended European Search Report for European Patent Application No. 20178880.9 dated Dec. 18, 2020.

Glonek, et al. "Hybrid Orientation Based Human Limbs Motion Tracking Method", Sensors, vol. 17, No. 12, Dec. 9, 2017, p. 2857.

Kok, et al. "Using Inertial Sensors for Position and Orientation Estimation", Foundations and Trends in Signal Processing: vol. 11, No. 1-2, Apr. 20, 2017.

Kaczmarek, et al. "IMU-based kinematic chain pose estimation using Extended Kalman Filter", Advances in Cooperative Robotics: Proceedings of the 19th International Conference on CLAWAR 2016, Aug. 3, 2016, pp. 331-338.

Japanese Office Action for Japanese Patent Application No. 2019-108446 dated Jun. 7, 2022.

Japanese Notice of Allowance for Japanese Patent Application No. 2019-108446 dated Aug. 23, 2022.

* cited by examiner

INFORMATION PROCESSING DEVICE, INFORMATION PROCESSING METHOD, AND STORAGE MEDIUM

CROSS-REFERENCE TO RELATED APPLICATION

Priority is claimed on Japanese Patent Application No. 2019-108446, filed Jun. 11, 2019, the content of which is incorporated herein by reference.

BACKGROUND

Field of the Invention

The present invention relates to an information processing device, an information processing method, and a storage medium.

Description of Related Art

There are a method of calculating a joint torque or muscle tension from human motions measured by motion capture (Non-Patent Document 1) and a method of estimating a ground reaction force (GRF) and a ground reaction moment (GRM) which are applied to both feet (Non-Patent Document 2). Here, the GRF and GRM which are applied to each of the feet are referred to as an external force collectively.
Non-Patent Document 1: Y. Nakamura, K. Yamane, I. Suzuki, and Y. Fujita: "Dynamics Computation of Musculo-Skeletal Human Model Based on Efficient Algorithm for Closed Kinematic Chains," Proceedings of the 2nd International Symposium on Adaptive Motion of Animals and Machines, Kyoto, Japan, SaP-I-2, March 2003.
Non-Patent Document 2: R. Fluit, "Prediction of ground reaction forces and moments during various activities of daily living," Journal of Biomechanics, p. 9, 2014.

Examples of motion measurement means include optical motion capture and a method of measuring a human motion from acceleration and angular velocity measured by an inertial sensor (inertial measurement unit (IMU)) (hereinafter referred to as IMU motion capture). It is necessary to dispose sensors around an object in the optical motion capture, whereas the IMU motion capture is easy to process because measurement is completed by a wearable sensor alone, and makes it possible to perform measurement in various environments.

Insofar as a motion and an external force can be estimated considering the modeling of a human body as a rigid link model, it is possible to calculate a torque of each joint through inverse dynamics calculation. In a case where the number of points of contact in a single-leg support phase or the like is one, it is possible to uniquely calculate an external force. However, in the case of involving two or more points of contact in a double-leg support phase or the like, it is necessary to distribute an external force to each of the points of contact. There are countless methods of distributing an external force which make it possible to realize a measured motion, and a distribution problem has to be solved using some kind of method.

Previous research for estimating an external force using an IMU (Non-Patent Document 3) involves preparing external force distribution factors of the right and left feet in advance as a function of a gate cycle, and determining a method of distributing an external force. Such a method needs to measure a distribution factor tailored to an object operation in advance, and cannot be applied to anything other than the object operation.
Non-Patent Document 3: A. Karatsidis, G. Bellusci, H. Schepers, M. de Zee, M. Andersen, and P. Veltink, "Estimation of Ground Reaction Forces and Moments During Gait Using Only Inertial Motion Capture," Sensors, vol. 17, no. 12, p. 75, December 2016.

On the other hand, in the field of robot control, a method for solving this distribution using quadratic programming (QP) is proposed. The external force distribution problem of any motion can be uniquely solved by including the L2 norm of an external force as a regularization term in an objective function. There is a preceding example (Non-Patent Document 4) in which this method is applied to a human motion, and an external force and a joint torque are estimated from a motion measured by the optical motion capture. However, there is no example in which this method is applied to the IMU motion capture.
Non-Patent Document 4: M. L. Felis, K. Mombaur, and A. Berthoz, "An optimal control approach to reconstruct human gait dynamics from kinematic data," in 2015 IEEE-RAS 15th International Conference on Humanoid Robots (Humanoids), Seoul, South Korea, 2015.

SUMMARY

IMU motion capture is a technique for estimating motions of the whole body using an IMU attached to each area of the body (hereinafter referred to as a segment). In this technique, processing is performed with data for a dimension of position represented in a generalized coordinate system as a starting point. However, for example, acceleration obtained by second-order differentiating the data for a dimension of position is smoothed, and thus information of a high-frequency component is often lost. For this reason, in the previous IMU motion capture, data of high-accuracy acceleration may not be able to be reflected in processing.

The present invention was contrived in view of such circumstances, and one object thereof is to provide an information processing device, an information processing method, and a storage medium that make it possible to obtain data for a dimension of acceleration having an improvement in followability to a high-frequency operation.

The following configurations are adopted in an information processing device, an information processing method, and a storage medium according to this invention.

(1) According to an aspect of this invention, there is provided an information processing device including: a storage device having a program stored therein; and a hardware processor, wherein the hardware processor executes the program stored in the storage device to: acquire first data for a dimension of position relating to an object represented in a generalized coordinate system; acquire at least second data for a dimension of acceleration from a plurality of inertial sensors attached to the object; and convert the second data into third data for a dimension of acceleration represented in the generalized coordinate system on the basis of the first data.

(2) In the aspect of the above (1), the hardware processor executes the program to derive a transformation rule on the basis of the first data, and converts the second data into the third data by applying the transformation rule to the second data.

(3) In the aspect of the above (1), the object is defined as including a plurality of segments and a joint that links two or more of the segments, and the generalized coordinate system includes at least a rotation angle around one or more axes for each joint as a variable.

(4) In the aspect of the above (3), the hardware processor executes the program to estimate at least one of an external force acting on the object and a torque which is generated in the joint on the basis of the first data, fourth data for a dimension of speed relating to the object obtained by differentiating the first data, and the third data.

(5) In the aspect of the above (4), the hardware processor executes the program to estimate at least one of the external force acting on the object and the torque which is generated in the joint by performing one or both of forward dynamics calculation and inverse dynamics calculation.

(6) According to another aspect of the present invention, there is provided an information processing method including causing a computer to: acquire first data for a dimension of position relating to an object represented in a generalized coordinate system; acquire at least second data for a dimension of acceleration from a plurality of inertial sensors attached to the object; and convert the second data into third data for a dimension of acceleration represented in the generalized coordinate system on the basis of the first data.

(7) According to another aspect of the present invention, there is provided a storage medium having a program stored therein, the program causing a computer to: acquire first data for a dimension of position relating to an object represented in a generalized coordinate system; acquire at least second data for a dimension of acceleration from a plurality of inertial sensors attached to the object; and convert the second data into third data for a dimension of acceleration represented in the generalized coordinate system on the basis of the first data.

According to the aspects of the above (1) to (7), it is possible to obtain data for a dimension of acceleration having an improvement in followability to a high-frequency operation.

DESCRIPTION OF EMBODIMENTS

Hereinafter, an embodiment of an information processing device, an information processing method, and a storage medium of the present invention will be described with reference to the accompanying drawings.

In the present specification, a vector q is expressed by [ ] as [q], a matrix T is expressed by < > as <T>, first-order differentiation of the vector q is expressed as [q]', and second-order differentiation is expressed as [q]" (however, except Expression (2)).

An information processing device is a device that acquires at least data for a dimension of acceleration from a plurality of inertial sensors (IMU sensors) attached to an object such as a human body, acquires data for a dimension of position relating to an object represented in a generalized coordinate system, and converts data of an acceleration into data for a dimension of acceleration represented in the generalized coordinate system on the basis of data for a dimension of position relating to an object represented in the generalized coordinate system, or estimates at least one of an external force acting on an object and a torque which is generated in the joint of the object on the basis of the conversion result. The data for a dimension of position includes both translational displacement and a rotation angle.

An object is not limited to a human body insofar as it includes segments (things that may be considered to be rigid bodies such as an arm, a hand, a leg, a foot, and the like in analytical mechanics, in other words, links) and a joint that links two or more segments. In the following description, a human body that is an object is referred to as a "target," and a plurality of inertial sensors are assumed to be attached to parts on a human body.

Figure 1:
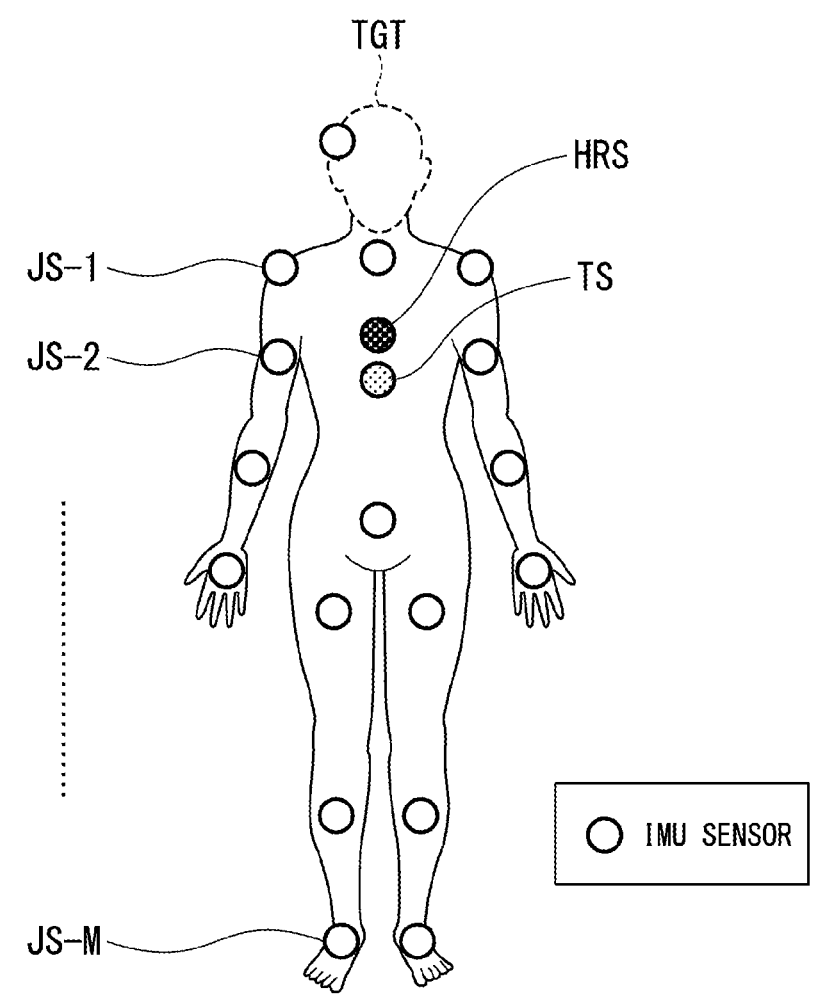
FIG. 1 is a diagram illustrating a state in which a plurality of IMU sensors are attached to a target.

FIG. 1 is a diagram illustrating a state in which a plurality of IMU sensors JS-k (k=1 to M) are attached to a target TGT. Each of the IMU sensors JS-k is a sensor that can measure an acceleration and an angular velocity in three axes in common. The IMU sensor JS-k is attached to a member (an IMU suit) such as, for example, detachable clothes, and the IMU sensor JS-k is positioned at a desired position by the target TGT wearing the member. For example, the IMU sensors JS-k are disposed such that an IMU sensor JS-1 is disposed at the right shoulder, an IMU sensor JS-2 is disposed at the right upper arm, an IMU sensor JS-8 is disposed at the left thigh, and an IMU sensor JS-9 is disposed below the left knee. A heart rate sensor HRS, a temperature sensor TS, or the like may also be attached to the IMU suit.

First Embodiment

Figure 2:
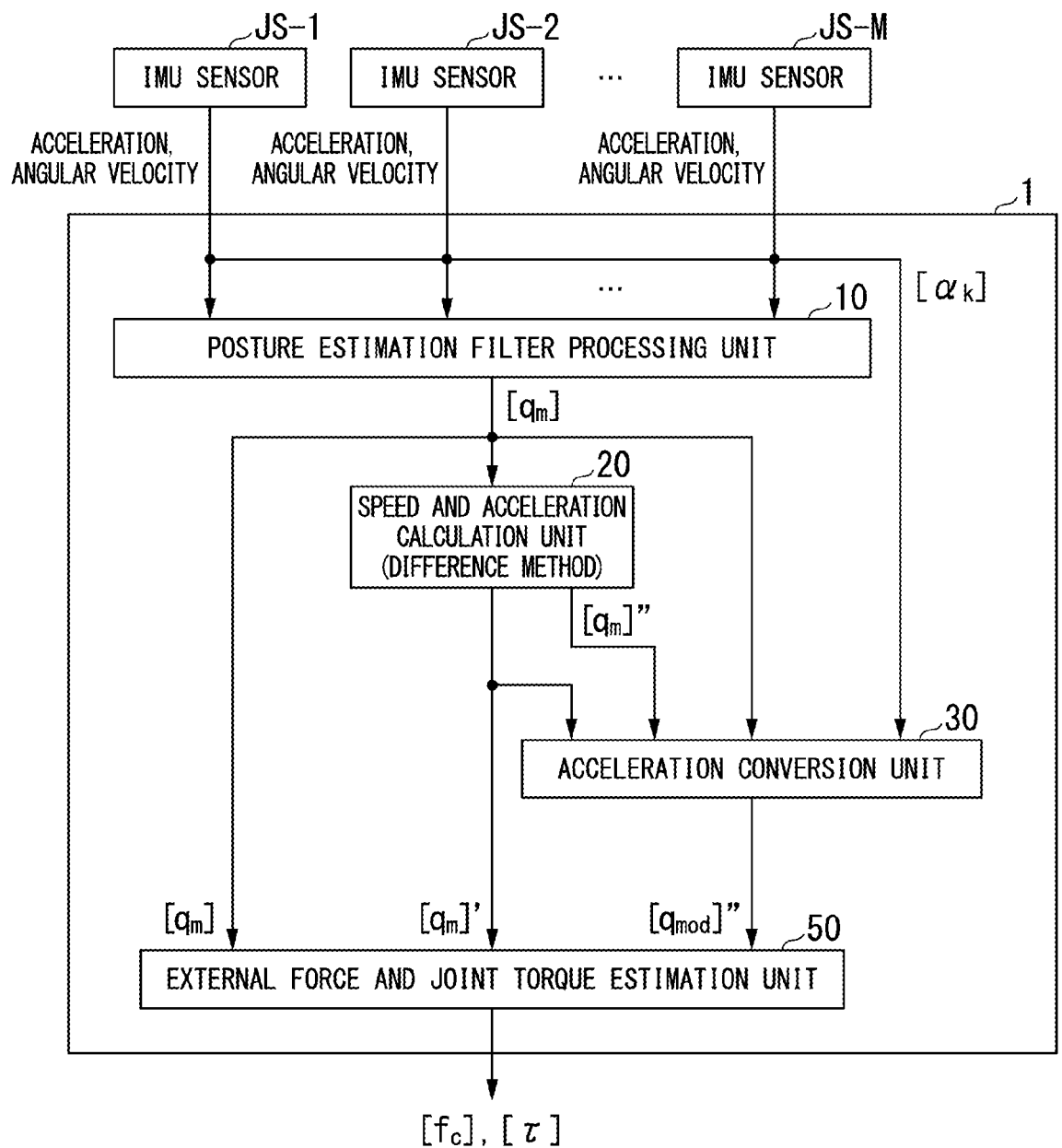
FIG. 2 is a configuration diagram of an information processing device according to an embodiment.

FIG. 2 is a configuration diagram of an information processing device 1 according to an embodiment. The information processing device 1 includes, for example, a posture estimation filter processing unit 10, a speed and acceleration calculation unit 20, an acceleration conversion unit 30, and an external force and joint torque estimation unit 50. Some or all of these components are realized by a hardware processor such as, for example, a central processing unit (CPU) executing a program (software). Some or all of these components may be realized by hardware (a circuit unit; including circuitry) such as a large scale integration (LSI), an application specific integrated circuit (ASIC), a field-programmable gate array (FPGA), or a graphics processing unit (GPU), and may be realized by software and hardware in cooperation. The program may be stored in advance in a storage device such as a hard disk drive (HDD) or a flash memory (a storage device including a non-transitory storage medium), may be stored in a detachable storage medium such as a DVD or a CD-ROM (a non-transitory storage medium), or may be installed by a storage medium being mounted in a drive device.

The posture estimation filter processing unit 10 generates data for a dimension of position relating to the target TGT (first data) represented in the generalized coordinate system on the basis of outputs of the IMU sensors JS-k. The posture estimation filter processing unit 10 is an example of a configuration for acquiring the first data. The information processing device 1 is another example of a configuration for acquiring the first data, and may include a unit that acquires data for a dimension of position generated by optical motion capture. The posture estimation filter processing unit 10 generates data for a dimension of position relating to the target TGT represented in the generalized coordinate system using, for example, a means referred to as an articulated human filter (AHF).

Figure 3:
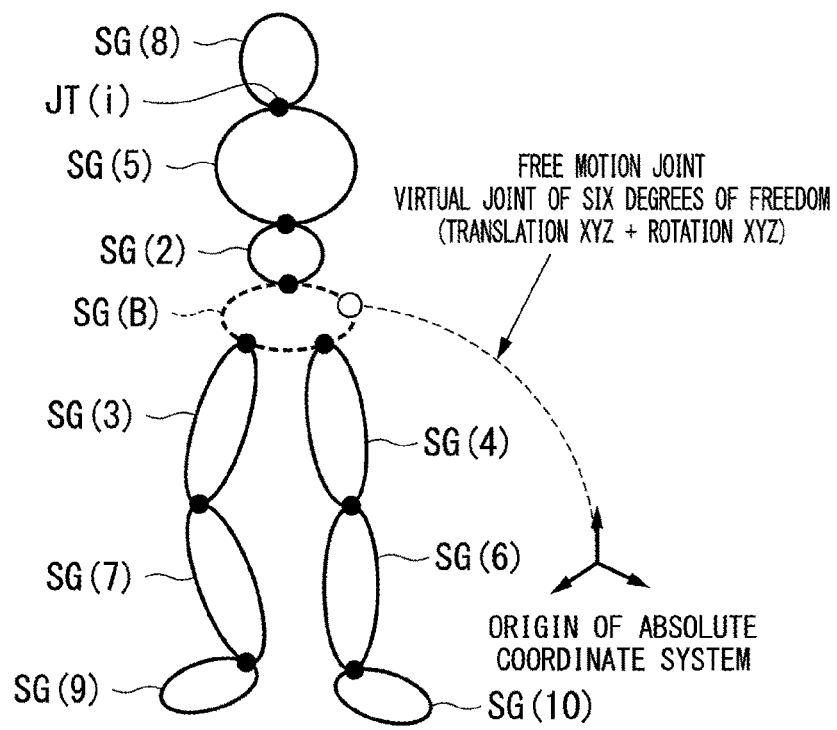
FIG. 3 is a diagram illustrating a generalized coordinate system in the embodiment.

Here, a generalized coordinate system will be described. The generalized coordinate system is a coordinate system in which, in a case where the target TGT is formed as a model, the posture of the target TGT can be represented depending on a variable according to the degree of freedom of the model. FIG. 3 is a diagram illustrating a generalized coordinate system in the embodiment. The generalized coordinate system in the present embodiment is a system in which, for example, the head, the breast, the abdomen, the pelvis, the right and left thighs, the right and left shins, and the right and left feet are classified into segments SG, and a joint JT(i) that links the segments is defined (i=1 to N). A segment SG(B) equivalent to the pelvis among the segments SG is defined as a base segment. The displacement of six degrees of freedom of segments other than the base segment with respect to the origin of an absolute coordinate system is not set as a variable of the generalized coordinate system, and only the base segment is treated as being displaceable in six degrees of freedom. The six degrees of freedom include three directions of translation (XYZ) and three directions of rotation (yaw, roll, and pitch).

The posture of the target TGT represented in the generalized coordinate system (hereinafter referred to as a "generalized position") [$q_m$] is a collection of variables having a dimension of position, and is represented by, for example, Expression (1). In the expression, [$q_0$] is a vector having a total of seven elements in four elements of a quaternion indicating the X coordinate, Y coordinate, Z coordinate, and posture of the base segment SG(B). In addition, [$q_i$] is a vector of a rotation angle having the number of dimensions according to the degree of freedom for each joint JT(i) (i=1 to N). For example, in the case of a joint equivalent to the knee, the vector is defined as having two degrees of freedom of the bending direction of the knee and the torsion direction of the shin, and thus is represented by a two-dimensional vector. In the case of a joint equivalent to the hip joint, the vector is defined as having three degrees of freedom, and thus is represented by a three-dimensional vector.

$$[q_m] = \{[q_0]^T, [q_1]^T, \ldots [q_i]^T, \ldots [q_N]^T\} \quad (1)$$

Figure 4:
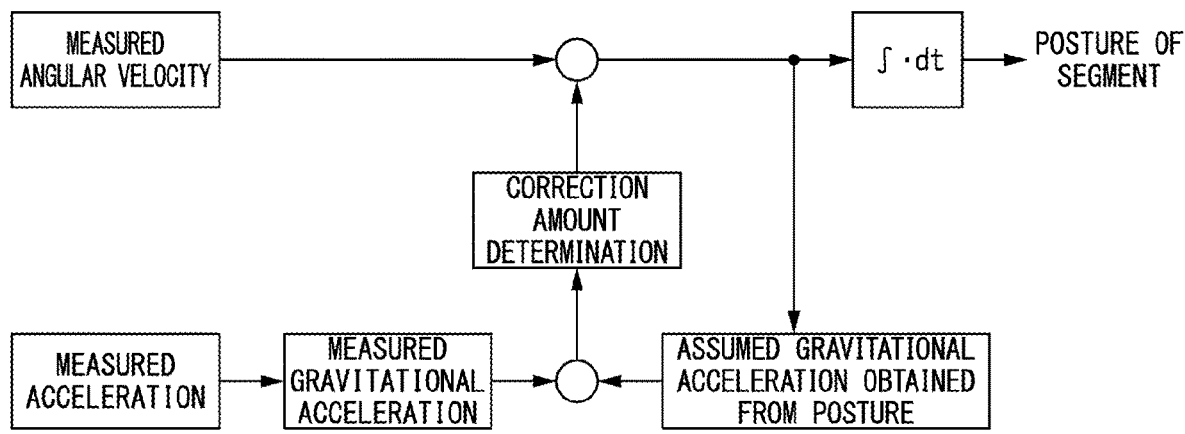
FIG. 4 is a diagram illustrating an example of processing details of a posture estimation filter processing unit.

Processing performed by the posture estimation filter processing unit 10 will be described in more detail. The processing performed by the posture estimation filter processing unit 10 is not specifically restricted, and any of the methods exemplified below may be adopted therein. As a simple example, the posture estimation filter processing unit 10 may calculate the posture of the segment SG (a yaw angle, a roll angle, and a pitch angle) by integrating the value of angular velocity measured by an IMU sensor JS-i, and perform a process using a method of correcting a measurement error of the angular velocity by gravitational acceleration. FIG. 4 is a diagram illustrating an example of processing details of the posture estimation filter processing unit 10. The posture estimation filter processing unit 10 calculates the posture of the segment SG by performing integration after correcting the angular velocity measured by the IMU sensor JS-i. The posture estimation filter processing unit 10 obtains a gravitational acceleration from the posture of the segment SG (assumed gravitational acceleration), and determines the amount of correction of the measured angular velocity in the direction of reducing deviation from gravitational acceleration (measured gravitational acceleration) measured by the IMU sensor JS-i.

The posture estimation filter processing unit 10 may perform posture estimation using a Madgwick filter. A Madgwick filter is a means for representing a posture in a quaternion and performing posture estimation at a high speed and with a high degree of accuracy by performing the correction of angular velocity using a gradient descent method. In the Madgwick filter, the posture estimation is performed by solving an optimization problem represented by Expression (2).

$$\min_{{}^S_E\hat{q}\in\mathbb{R}^4} \frac{1}{2}\|f({}^S_E\hat{q}, {}^E\hat{d}, {}^S\hat{s})\|^2 \quad (2)$$

$$f({}^S_E\hat{q}, {}^E\hat{d}, {}^S\hat{s}) = {}^S_E\hat{q}^* \otimes {}^E\hat{d} \otimes {}^S_E\hat{q} - {}^S\hat{s}$$

Figure 5:
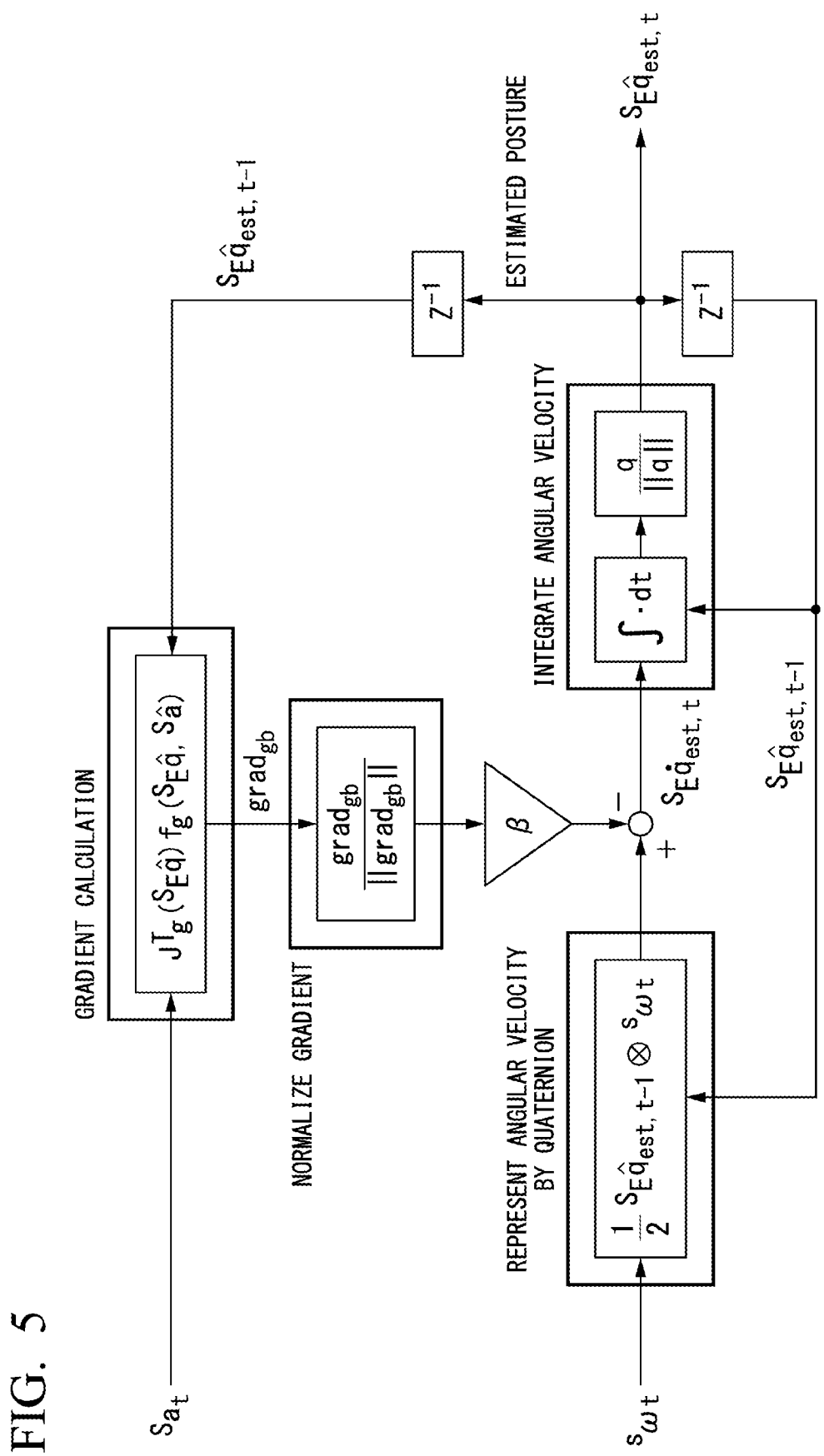
FIG. 5 is a diagram illustrating another example of processing details of the posture estimation filter processing unit.

The argument (${}^S_E$q hat) of a function f is an estimated posture of the IMU sensor JS-I in a sensor coordinate system, the argument (${}^E$d hat) is a reference direction of gravity, geomagnetism or the like in a world coordinate system, and the argument (${}^S$s hat) is a measurement value of gravity, geomagnetism or the like in the sensor coordinate system. The processing performed by the posture estimation filter processing unit 10 in a case where the Madgwick filter is used is represented in FIG. 5. FIG. 5 is a diagram illustrating another example of processing details of the posture estimation filter processing unit 10. As shown in the drawing, in a case where the Madgwick filter is used, the posture estimation filter processing unit 10 performs gradient calculation on the basis of a posture estimated by integrating angular velocity, and corrects an angular velocity on the basis of a value obtained by normalizing a gradient.

The posture estimation filter processing unit 10 may set a reference plane in the case of an object of which the rotation angle of the joint JT is restricted as in a human body, and correct an angular velocity on the basis of an angle between the normal line of the reference plane and the direction of each segment SG.

A generalized position [$q_m$] which is obtained by the various methods described above is output to the speed and acceleration calculation unit 20, the acceleration conversion unit 30, and the external force and joint torque estimation unit 50.

The speed and acceleration calculation unit 20 calculates, for example, a vector obtained by first-order differentiating the generalized position [$q_m$] (an example of fourth data; hereinafter referred to as a "generalized speed") [$q_m$]' and a vector obtained by second-order differentiating the generalized position [$q_m$] (hereinafter referred to as a "generalized acceleration") [$q_m$]" using a difference method (referring to dividing two values having different times by an elapsed time and obtaining the result) with respect to the generalized position [$q_m$] which is input in a time-series manner.

Data of acceleration (an example of second data) is input to the acceleration conversion unit 30 from each of the IMU sensors JS-k. Since one IMU sensor JS-k detects an acceleration on three axes, data of the acceleration becomes a three-dimensional vector $[\alpha_k]$. The generalized position $[q_m]$, the generalized speed $[q_m]'$, and the generalized acceleration $[qm]''$ are input to the acceleration conversion unit 30.

Figure 6:
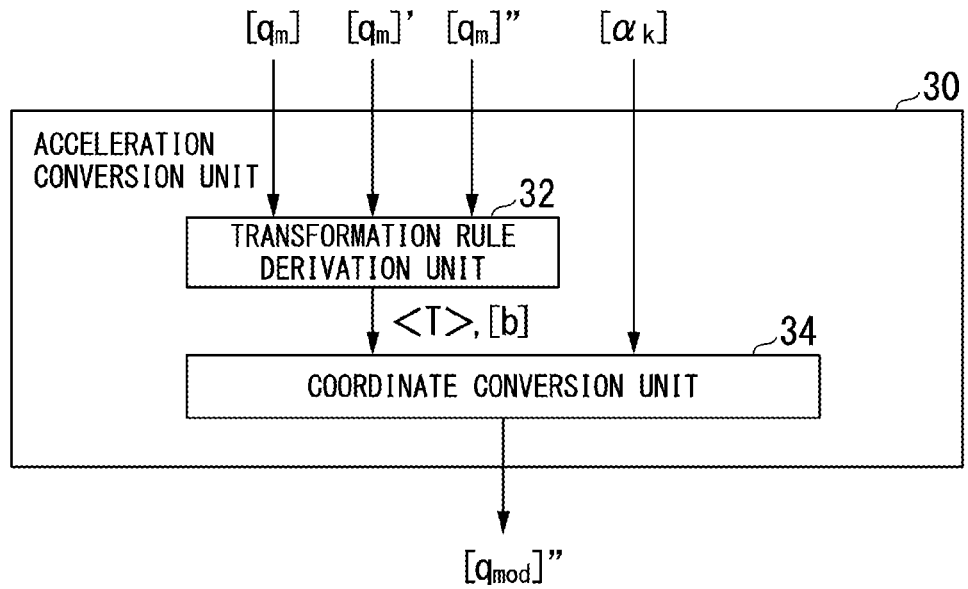
FIG. 6 is a configuration diagram of an acceleration conversion unit.

FIG. 6 is a configuration diagram of the acceleration conversion unit 30. The acceleration conversion unit 30 includes, for example, a transformation rule derivation unit 32 and a coordinate conversion unit 34.

The transformation rule derivation unit 32 derives a transformation matrix $<T>$ and a transformation vector $[b]$ from the result of processing performed by the posture estimation filter processing unit 10. The transformation matrix $<T>$ and the transformation vector $[b]$ are an example of a "transformation rule" which is applied to an acceleration vector.

The coordinate conversion unit 34 causes the transformation matrix $<T>$ and the transformation vector $[b]$ to act on (specifically multiply by) an acceleration vector $[\alpha]$, to thereby derive data for a dimension of acceleration (an example of third data; hereinafter referred to as a "modified generalized acceleration") $[q_{mmos}]''$ represented in the generalized coordinate system. Expression (3) is an example of the definitional equation of the acceleration vector $[\alpha]$. Herein, $[\alpha_k]$ is a vector having accelerations in three directions detected by the IMU sensor JS-k as elements. Expression (4) represents a method of deriving the modified generalized acceleration $[q_{mod}]''$. The modified generalized acceleration $[q_{mod}]''$ is information in which acceleration is described with respect to an element which is a translational position and angular acceleration is described with respect to an element which is a rotation angle.

$$[\alpha] = \{[\alpha_1]^T, [\alpha_2]^T, \ldots, [\alpha_M]^T\} \quad (3)$$

$$[q_m]'' = <T> \cdot [\alpha] + [b] \quad (4)$$

First Example

Hereinafter, a method of deriving the transformation matrix $<T>$ and the transformation vector $[b]$ will be described. In a case where the number of dimensions of the modified generalized acceleration $[q_{mmos}]''$ is set to L, and the number of dimensions of the acceleration vector $[\alpha]$ is set to K, the transformation rule derivation unit 32 derives an L×K transformation matrix $<T>$ and an L-dimensional transformation vector $[b]$ as shown in Expression (5). In the expression, $<T_0>$ is a transformation matrix corresponding to rotation and translational acceleration of the base segment, and is a 6×K matrix. A matrix $<T_i>$ (i=1 to N) corresponds to the angular acceleration of a joint JT-i. In a case where the degree of freedom of the joint JT-i (the number of dimensions of a corresponding vector) is set to $P_i$, $<T_i>$ becomes a $P_i$×K matrix. A vector $[b_0]$ is a six-dimensional vector, and a vector $[b_i]$ (i=1 to N) is a $P_i$-dimensional vector. The reason that $[q_0]$ is a vector consisting of seven elements, whereas $<T_0>$ is a 6×K matrix, and $[b_0]$ is a six-dimensional vector is because a posture (rotation) is represented by a four-dimensional quaternion in a dimension of position, and is represented three-dimensionally in dimensions of speed and acceleration.

$$<T> = \begin{bmatrix} <T_0> \\ <T_1> \\ <T_2> \\ \vdots \\ <T_i> \\ \vdots \\ <T_{N-1}> \\ <T_N> \end{bmatrix}_{L \times K} \quad [b] = \begin{bmatrix} <b_0> \\ <b_1> \\ <b_2> \\ \vdots \\ <b_i> \\ \vdots \\ <b_{N-1}> \\ <b_N> \end{bmatrix}_{L \times 1} \quad (5)$$

In a case where the generalized position $[q_m]$ is given, the sensor coordinate system speed $[v]$ of the IMU sensor JS-k can be represented by Expression (6) using a Jacobian matrix $<J_i>$. In this expression, the generalized speed is mapped to the speed of the IMU sensor JS-k. Here, $[q_i]$ is a vector (a scalar in the case of one degree of freedom) indicating an element for each joint included in the generalized position $[q_m]$.

$$[v] = <J_i> \cdot [q_i]' \quad (6)$$

When Expression (6) is arranged for $[q_i]''$ by performing time differentiation, Expressions (7) and (8) are obtained. Here, a matrix $<J_i\#>$ is a pseudo inverse matrix of the matrix $<J_i>$.

$$[\alpha] = <J_i>' \cdot [q_i]' + <J_i> \cdot [q_i]'' \quad (7)$$

$$[qi]'' = <J_i\#> \cdot ([\alpha] - <J_i>' \cdot [q_i]') \quad (8)$$

From the above relation, the transformation rule derivation unit 32 derives $<T_i>$ and $[b_i]$ on the basis of Expressions (9) and (10).

$$<T_i> = <J_i\#> \quad (9)$$

$$[bi] = -<J_i\#> \cdot <J_i>' \cdot [q_m] \quad (10)$$

Second Example

The transformation rule derivation unit 32 may derive the transformation matrix $<T>$ and the transformation vector $[b]$ using simpler calculation to be described below. In this method, $<T_0>$ and $[b_0]$ are represented by Expressions (11) and (12). In the expressions, $<R_0>$ is a 3×3 rotation matrix in which the acceleration of a sensor coordinate system measured by the IMU sensor is converted into an absolute coordinate system. In addition, $<0>$ is a matrix in which all elements are zero. In addition, $\omega_x'$, $\omega_y'$, and $\omega_z'$ are angular accelerations around the X-axis, Y-axis, and Z-axis of the base segment, respectively, calculated using a difference method.

$$<T_0> = \begin{bmatrix} <0> & <0> & <0> & \ldots & <0> \\ <R_0> & <0> & <0> & \ldots & <0> \end{bmatrix} \quad (11)$$

$$[b_0] = [\omega_x', \omega_y', \omega_z', 0, 0, 0, 0]^T \quad (12)$$

In this case, the transformation rule derivation unit 32 may derive $<T_i>$ and $[b_i]$ on the basis of Expressions (13) and (14). As a result, for i=1 to N, the i-th element of the modified generalized acceleration $[q_{mod}]''$ uses the i-th element of the generalized acceleration $[q_m]''$ as it is.

$$<T_i>=<0> \quad (13)$$

$$[b_i]=\text{i-th element of } [q_m]'' \quad (14)$$

Using the above-described method, the acceleration conversion unit 30 generates data for a dimension of acceleration in the generalized coordinate system on the basis of outputs of the IMU sensors JS-k that measure an acceleration in the sensor coordinate system. Therefore, it is possible to obtain higher-accuracy data for a dimension of acceleration than in a case where the data for a dimension of acceleration is generated, for example, by second-order differentiating the generalized position [qm] using a difference method.

The external force and joint torque estimation unit 50 estimates an external force and a joint torque on the basis of the generalized position $[q_m]$, the generalized speed $[q_m]'$, and the modified generalized acceleration $[q_{mod}]''$ which are generated as described above.

The external force and joint torque estimation unit 50 estimates an external force and a joint torque by solving, for example, an objective function represented by Expression (15) and an optimization problem caused by a restriction represented by Expression (16).

$$\text{Objective function: } \min_{[fc]} \frac{1}{2}(\|[q]'' - [q_{mod}]''\|^2 + \mu \cdot \|[f_c]\|^2) \quad (15)$$

$$\text{Restrictions: } [n_z^T] \cdot [f_{c,j}] > 0, \quad (16)$$
$$\mu \cdot [n_z^T] \cdot [f_{c,j}] - \|[f_{c,j}]\| - [n_z^T] \cdot [f_{c,j}] \cdot [n_z]\| > 0$$

In Expression (15), $[q]''$ is, for example, a calculated acceleration which is obtained in forward dynamics calculation shown in Expression (17). For the purpose of comparison with the calculated acceleration $[q]''$, the modified generalized acceleration $[q_{mod}]''$ which is output by the acceleration conversion unit 30 is referred to as a measured acceleration $[q_m]''$. Here, $\mu$ is a weight of a regularization term, $[\tau]$ is a joint torque, and $[f_c]$ is an external force. The joint torque $[\tau]$ is a vector in which a torque generated for each joint JT is used as an element.

$$[q]''=FD([q_m],[q_m]',[\tau],[f_c]) \quad (17)$$

Figure 7:
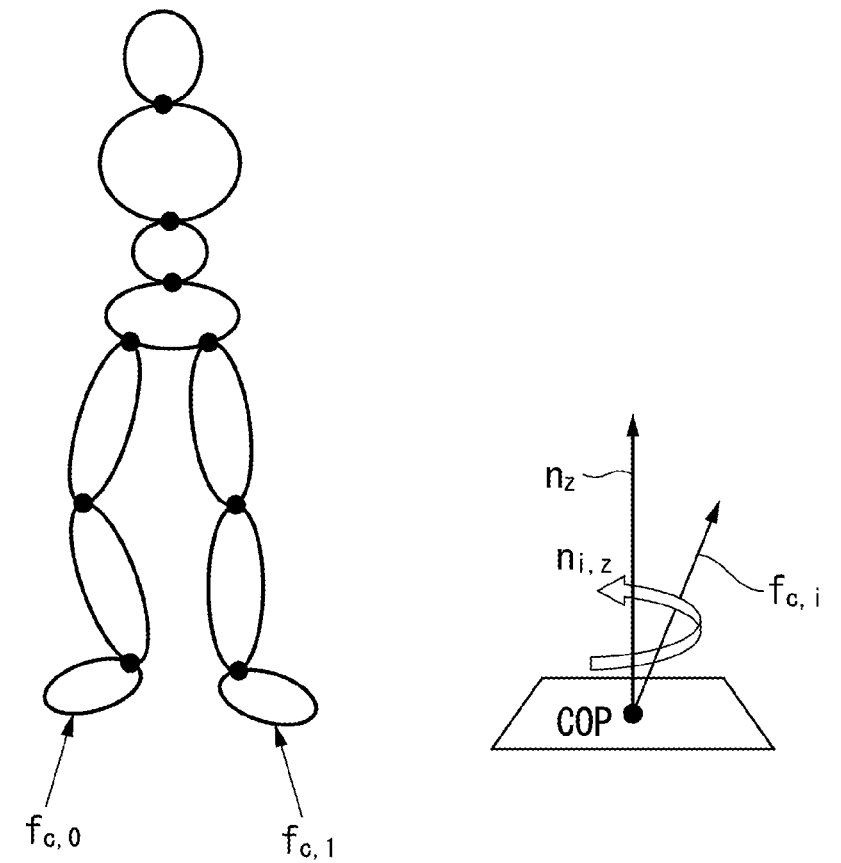
FIG. 7 is a diagram illustrating an external force.

FIG. 7 is a diagram illustrating an external force $[f_c]$. The external force acting on the target TGT which is treated in the present embodiment is assumed to be a reaction force (ground reaction force) which is received by only the right and left feet from the floor, the ground or the like. A ground reaction force which is applied to the right foot is defined as $[f_{c,0}]$, and a ground reaction force which is applied to the left foot is defined as $[f_{c,1}]$. An argument indicating either of the feet is set to j, and is generalized and shown as $[f_{c,j}]$. Here, $[f_{c,j}]$ is a vector in which a force applied to the contact surface of each foot is represented as a force acting on the center of pressure (COP) of one point, and is a four-dimensional vector including $f_{j,x}$, $f_{j,y}$, and $f_{j,z}$ which are three components of a force in a translational direction and a moment $n_{j,z}$ around a vertical axis (Z-axis). The external force $[f_c]$ is an eight-dimensional vector in which ground reaction forces applied to the right and left feet are linked to each other. The relational expressions thereof are shown in Expressions (6) and (7). The external force $[f_c]$ can be defined arbitrarily without being limited thereto.

$$[f_c] = \begin{bmatrix} [f_{c,0}] \\ [f_{c,1}] \end{bmatrix} \quad (18)$$

$$[f_{c,j}] = \{(f_{j,x}), (f_{j,y}), (f_{j,z}), (n_{j,z})\}^T \quad (19)$$

In the restrictions, $\{[n_z^T] \cdot [f_{c,j}] > 0\}$ means that the vertical component (Z direction component) of the external force $[f_{c,j}]$ is positive. Here, since an upward reaction force is set to be positive, this restriction means that the feet are not drawn by the floor or the ground.

Figure 8:
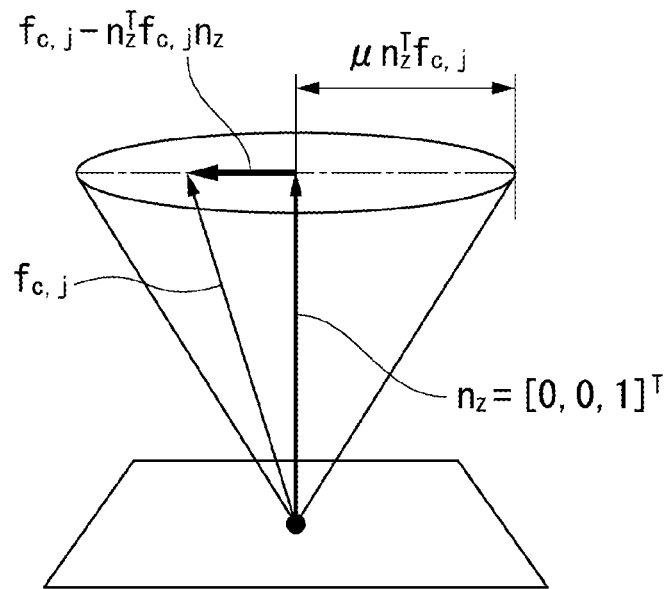
FIG. 8 is a diagram illustrating a restriction.

In the restrictions, $\{\mu \cdot [n_z^T] \cdot [f_{c,j}] - \|[f_{c,j}]\| - [n_z^T] \cdot [f_{c,j}] \cdot [n_z]\| > 0\}$ will be described with reference to FIG. 8. FIG. 8 is a diagram illustrating a restriction. Here, $[n_z]$ is an upward unit vector along a vertical axis. This restriction is a condition in which the direction of an external force is restricted so that a grounding point is not slippery against the ground having a coefficient of static friction $\mu$.

A portion of the restriction may be omitted. For example, in a case where the feet are assumed to be able to slip on the floor or the ground, the right term of the restriction may be omitted.

Hereinafter, functions which are executed by the external force and joint torque estimation unit 50 under the definition as stated above will be described. The external force and joint torque estimation unit 50 may directly perform forward dynamics calculation shown in Expression (17), and can perform more rapid processing by applying inverse dynamics calculation to some portions as will be described below. This is because when the external force $[f_c]$ is determined, the joint torque $[\tau]$ can be calculated in inverse dynamics using the measured joint acceleration.

Figure 9:
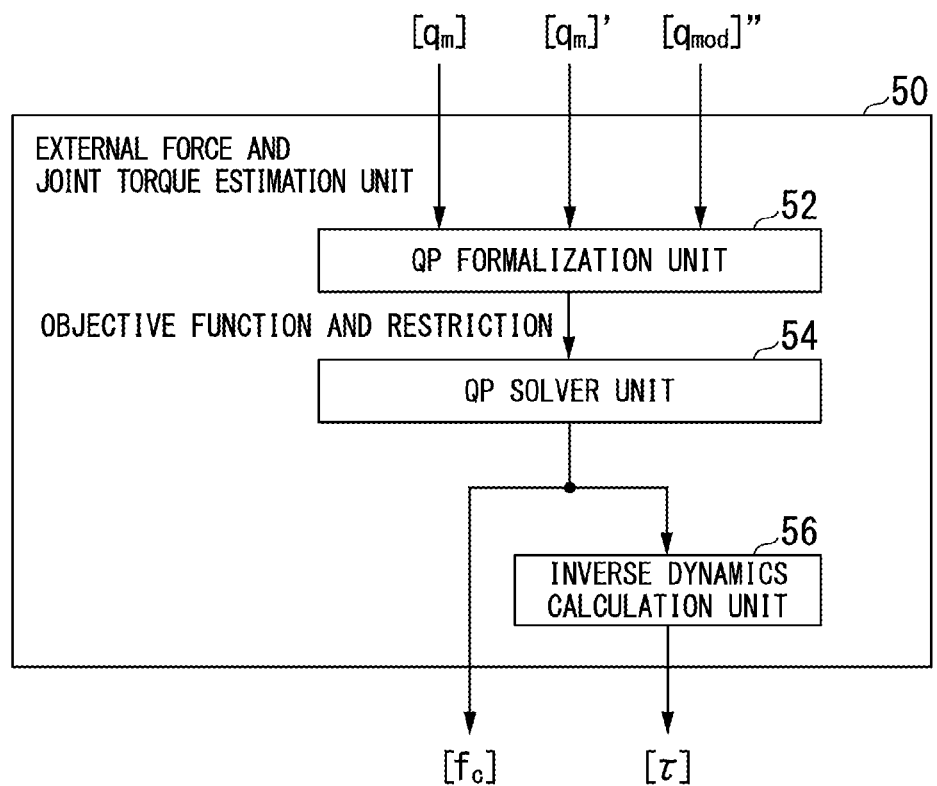
FIG. 9 is a configuration diagram of an external force and joint torque estimation unit.

FIG. 9 is a configuration diagram of the external force and joint torque estimation unit 50. The external force and joint torque estimation unit 50 includes, for example, a QP formalization unit 52, a QP solver unit 54, and an inverse dynamics calculation unit 56.

The QP formalization unit 52 converts the forward dynamics calculation shown in Expression (17) into an objective function of a quadratic programming (QP) form shown in Expression (18). In the expression, a matrix $<Q>$ is a square matrix having the same degree as the external force [fc], and [c] is a vector having the same degree as the external force [fc].

$$\min_{[fc]} \frac{1}{2} [fc]^T \cdot \langle Q \rangle \cdot [fc] + [c]^T \cdot [fc] \quad (20)$$

The QP solver unit 54 calculates the external force $[f_c]$ by solving an objective function converted into a QP form by the QP formalization unit 52 using a sequential quadratic programming method or an adduction method.

The inverse dynamics calculation unit 56 performs the inverse dynamics calculation shown in Expression (19) using the external force $[f_c]$ calculated by the QP solver unit 54, and calculates the joint torque $[\tau]$. Here, [q] is a calculation position, and [q]' is a calculation speed.

$$[\tau]=ID([q],[q]',[q_m]'',[f_c]) \quad (19)$$

According to the first embodiment described above, the acquisition unit (10) that acquires data for a dimension of position relating to an object ($[q_m]$) represented in the generalized coordinate system and the conversion unit (30) that acquires at least data for a dimension of acceleration ($[\alpha_k]$) from a plurality of inertial sensors (JS-k) attached to the object and converts the acquired data of acceleration into data for a dimension of acceleration ($[q_m]''$) represented in the generalized coordinate system on the basis of data for a dimension of position relating to the object represented in the generalized coordinate system are included, whereby, it is possible to obtain data for a dimension of acceleration having a further improvement in followability to a high-frequency operation than in a case where the data for a dimension of acceleration represented in the generalized coordinate system is obtained by the data for a dimension of position relating to the object ($[q_m]$) represented by second-order differentiating the generalized coordinate system using a difference method.

Figure 10:
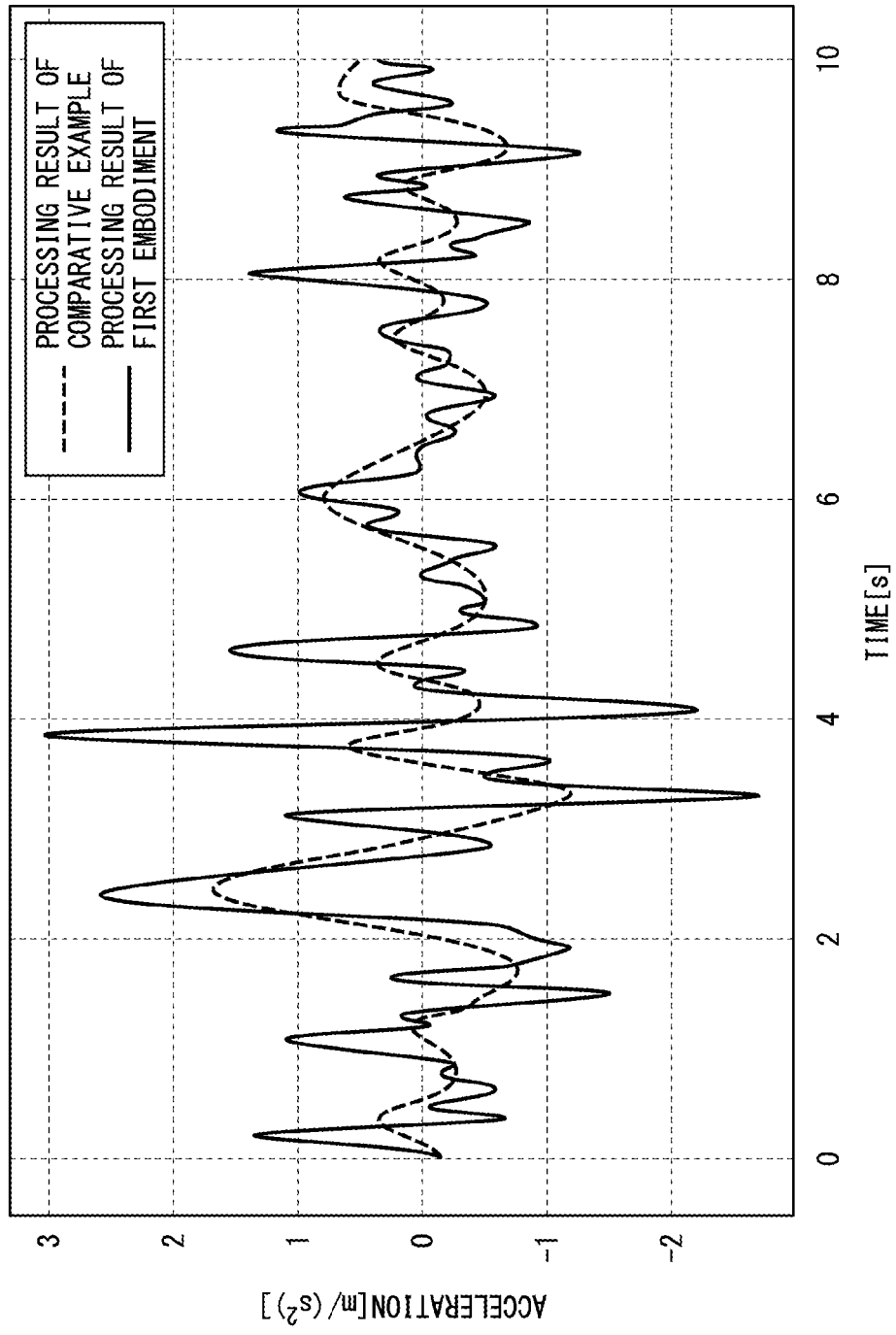
FIG. 10 is a diagram in which data for a dimension of acceleration (processing results) which is generated by an information processing device of a comparative example and an information processing device having an acceleration conversion unit of a first embodiment is compared.

Hereinafter, the results of an experiment performed by the inventor of the present application will be described. FIG. 10 is a diagram in which data for a dimension of acceleration (processing results) which is generated by an information processing device of a comparative example and the information processing device 1 having the acceleration conversion unit 30 of the first embodiment is compared. The information processing device of a comparative example "obtains data for a dimension of acceleration represented in the generalized coordinate system by second-order differentiating the data for a dimension of position relating to an object ($[q_m]$) represented in the generalized coordinate system using a difference method." As shown in the drawing, the processing results of the first embodiment show that the degree of smoothing a waveform is suppressed more than in the comparative example, and that it is also possible to follow the magnitude of a peak with a good degree of accuracy. Therefore, according to the first embodiment, it is possible to improve followability to a high-frequency operation.

According to the first embodiment, the estimation unit (50) that estimates at least one of an external force acting on an object and a torque generated in the joint on the basis of data for a dimension of position ($[q_m]$) represented in the generalized coordinate system, data for a dimension of speed relating to the object ($[q_m]'$) obtained by differentiating the data for a dimension of position, and data for a dimension of acceleration ($[q_m]''$) converted by the conversion unit (30) is further included, whereby it is possible to obtain estimation results having an improvement in followability to a high-frequency operation.

Second Embodiment

Hereinafter, a second embodiment will be described. The objective function in the first embodiment is represented by Expression (15), but an objective function in the second embodiment is represented by Expression (21). In the expression, $[q_{mbase}]''$ is a measured acceleration of the base segment SG(B) (another example of data of acceleration represented in the generalized coordinate system), and $[q_{base}]''$ is a calculated acceleration of the base segment SG(B). They are all vectors having the same elements as $[q_0]$ described in the first embodiment, that is, total seven elements in four elements of a quaternion indicating the X coordinate, Y coordinate, Z coordinate, and posture of the base segment SG(B). Restrictions are the same as those in the first embodiment.

$$\text{Objective function: } \min_{[f_c],[\tau]} \frac{1}{2}(\|[q_{base}]'' - [q_{mbase}]''\|^2 + \mu \cdot \|[f_c]\|^2) \quad (21)$$

$$\text{Restrictions: } [n_z^T] \cdot [f_{c,j}] > 0, \quad (22)$$
$$\mu \cdot [n_z^T] \cdot [f_{c,j}] - \|[f_{c,j}] - [n_z^T] \cdot [f_{c,j}] \cdot [n_z]\| > 0$$

The acceleration conversion unit 30 of the second embodiment calculates a measured acceleration $[q_m]''$ by causing a transformation matrix <T> obtained similarly to the first embodiment to act on an input vector $[\alpha_k]$ and outputs the calculated measured acceleration to the external force and joint torque estimation unit 50. The external force and joint torque estimation unit 50 of the second embodiment performs calculation by extracting $[q_{mbase}]''$ from the measured acceleration $[q_m]''$.

The external force and joint torque estimation unit 50 of the second embodiment performs inverse dynamics calculation shown in Expression (23), and calculates the calculated acceleration $[q_{base}]''$ and the joint torque τ. Here, $[q_m\#]''$ is a vector in which $[q_{mbase}]''$ is excluded from $[q_m]''$. HD( ) is a calculation means in which forward dynamics calculation and inverse dynamics calculation are mixed with each other by switching between the forward dynamics calculation and the inverse dynamics calculation for each segment.

$$[\tau],[q_{base}]''=HD([q_m],[q_m]',[q_m\#]'',[f_c]) \quad (23)$$

Figure 11:
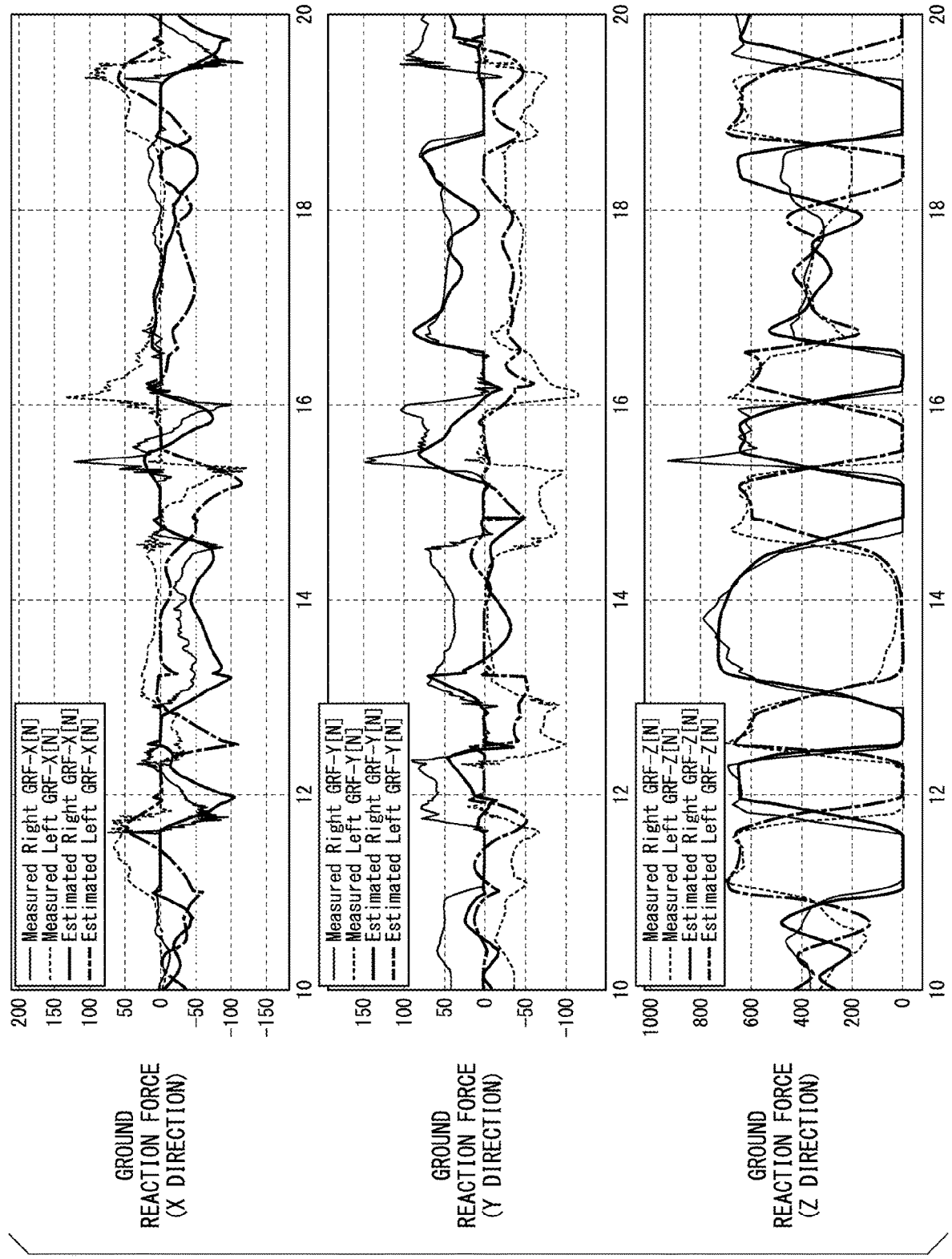
FIG. 11 is a diagram illustrating processing results of the information processing device of a comparative example.

By performing the above processing, it is possible to obtain the same results with a smaller number of calculations than in the first embodiment. Hereinafter, the results of an experiment performed by the inventor of the present application will be described. FIG. 11 is a diagram illustrating processing results of the information processing device of a comparative example. The information processing device of a comparative example "obtains generalized acceleration of the base segment SG(B) by second-order differentiating the generalized position of the base segment SG(B) using a difference method." In the drawing, "Measured right" is a measured reaction force having acted on the right foot. The measured reaction force is a force measured by a pressure sensor attached to the floor. "Measured left" is a measured reaction force having acted on the left foot. "Estimated right" is an estimated reaction force (external force) estimated to have acted on the right foot by the information processing device of the comparative example, and "Estimated left" is an estimated reaction force (external force) estimated to have acted on the left foot by the information processing device of the comparative example.

Figure 12:
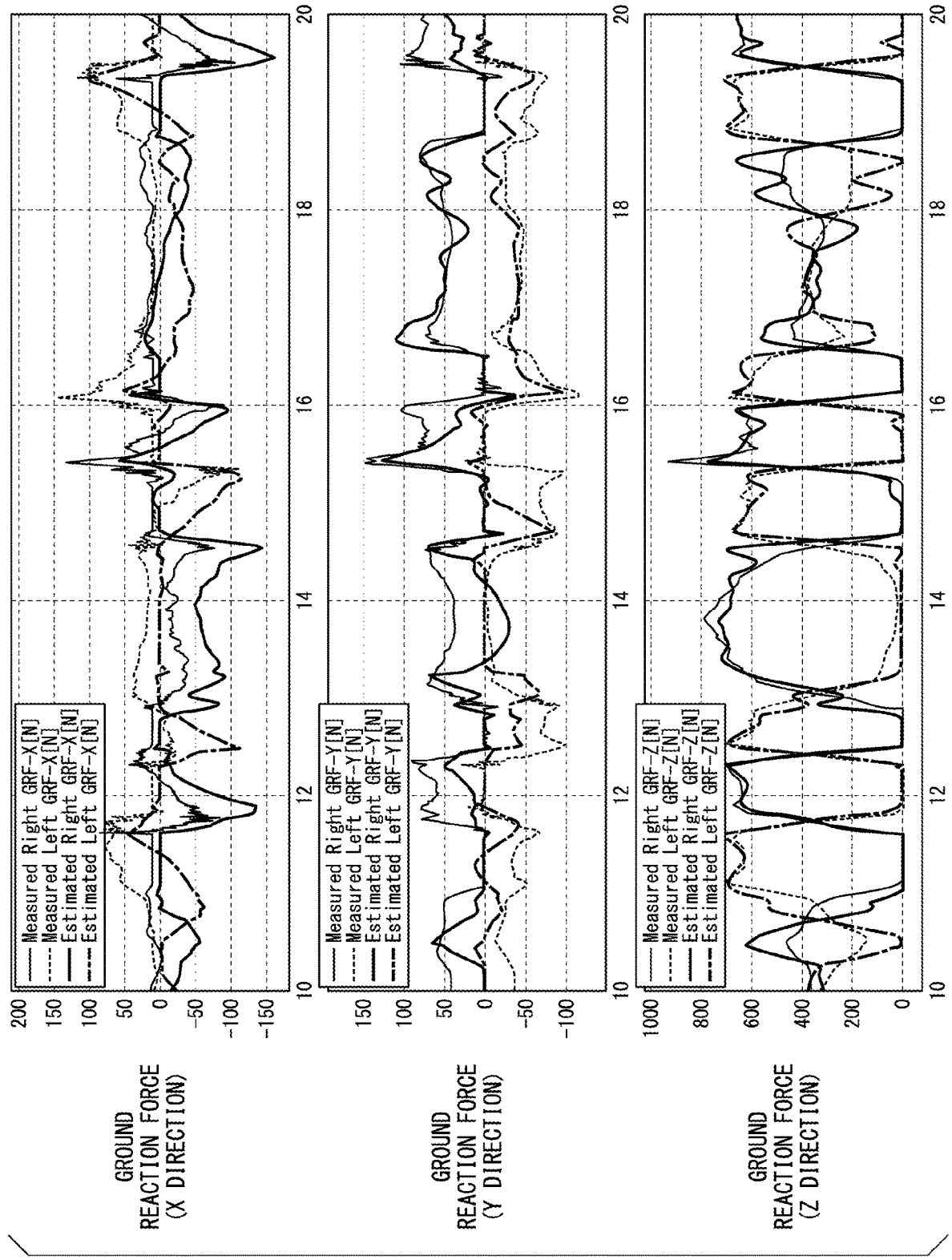
FIG. 12 is a diagram illustrating processing results of an information processing device of a second embodiment.

FIG. 12 is a diagram illustrating processing results of the information processing device 1 of the second embodiment. In the drawing, "Measured right" and "Measured left" are the same as those in FIG. 11. "Estimated right" is an estimated reaction force (external force) estimated to have acted on the right foot by the information processing device 1 of the second embodiment, and "Estimated left" is an estimated reaction force (external force) estimated to have acted on the left foot by the information processing device 1 of second embodiment.

As understood when FIG. 11 and FIG. 12 are compared with each other, the processing results of the information processing device 1 of the second embodiment show that the degree of smoothing a waveform is suppressed, and that it is also possible to follow the magnitude of a peak with a good degree of accuracy. The root mean squares (RMS) of the measured reaction force and the estimated reaction force of the comparative example become significant larger. Therefore, according to the second embodiment, it is possible to improve followability to a high-frequency operation.

According to the second embodiment described above, it is possible to exhibit the same effect with a smaller number of calculations than in the first embodiment.

In each embodiment described above, although the generation of data for a dimension of position relating to the target TGT represented in the generalized coordinate system on the basis of outputs of the IMU sensors and the acquisition of data for a dimension of position generated by the optical motion capture have been exemplified, data may be acquired from both of them. In this case, for example, a transformation matrix may be calculated on the basis of the data for a dimension of position generated by the optical motion capture, and be caused to act on data for a dimension of acceleration included in the outputs of the IMU sensors.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An information processing device comprising:
    a storage device having a program stored therein; and
    a hardware processor,
    wherein the hardware processor executes the program stored in the storage device to:
        acquire first data having a dimension of position of an object represented in a generalized coordinate system, wherein the object is a human body and defined as including a plurality of segments and a joint that links two or more of the segments, the plurality of segments include a left foot and a right foot in the human body, and the joint is a knee in the human body, and the generalized coordinate system includes at least a rotation angle around one or more axes for each joint as a variable;
        acquire at least second data having a dimension of acceleration from a plurality of inertial sensors attached to the plurality of segments and the joint of the object;
        derive a transformation rule on the basis of the first data;
        convert the second data into third data having a dimension of acceleration represented in the generalized coordinate system by applying the derived transformation rule to the second data; and
        estimate a torque which is generated in the joint, a first ground reaction force which is applied to the left foot, and a second ground reaction force which is applied to the right foot on the basis of the first data, fourth data having a dimension of speed relating to the object obtained by differentiating the first data, and the third data.

2. The information processing device according to claim 1, wherein the hardware processor further executes the program to estimate the torque which is generated in the joint, the first ground reaction force, and the second ground reaction, by performing one or both of a forward dynamics calculation and an inverse dynamics calculation.

3. An information processing method comprising causing a computer to:
    acquire first data having a dimension of position of an object represented in a generalized coordinate system, wherein the object is a human body and defined as including a plurality of segments and a joint that links two or more of the segments, the plurality of segments include a left foot and a right foot in the human body, and the joint is a knee in the human body, and the generalized coordinate system includes at least a rotation angle around one or more axes for each joint as a variable;
    acquire at least second data having a dimension of acceleration from a plurality of inertial sensors attached to the plurality of segments and the joint of the object;
    derive a transformation rule on the basis of the first data;
    convert the second data into third data having a dimension of acceleration represented in the generalized coordinate system by applying the derived transformation rule to the second data; and
    estimate a torque which is generated in the joint, a first ground reaction force which is applied to the left foot, and a second ground reaction force which is applied to the right foot on the basis of the first data, fourth data having a dimension of speed relating to the object obtained by differentiating the first data, and the third data.

4. A computer readable non-transitory storage medium having a program stored therein, the program causing a computer to:
    acquire first data having a dimension of position of an object represented in a generalized coordinate system, wherein the object is a human body and defined as including a plurality of segments and a joint that links two or more of the segments, the plurality of segments include a left foot and a right foot in the human body, and the joint is a knee in the human body, and the generalized coordinate system includes at least a rotation angle around one or more axes for each joint as a variable;
    acquire at least second data having a dimension of acceleration from a plurality of inertial sensors attached to the plurality of segments and the joint of the object;
    derive a transformation rule on the basis of the first data;
    convert the second data into third data having a dimension of acceleration represented in the generalized coordinate system by applying the derived transformation rule to the second data; and
    estimate a torque which is generated in the joint, a first ground reaction force which is applied to the left foot, and a second ground reaction force which is applied to the right foot on the basis of the first data, fourth data having a dimension of speed relating to the object obtained by differentiating the first data, and the third data.

* * * * *